(12) United States Patent
Esplin et al.

(10) Patent No.: US 10,517,995 B2
(45) Date of Patent: Dec. 31, 2019

(54) SUPER-HYDROPHOBIC MATERIALS AND ASSOCIATED DEVICES, SYSTEMS, AND METHODS

(71) Applicant: Brigham Young University, Provo, UT (US)

(72) Inventors: Christian D. Esplin, Provo, UT (US); Brian D. Jensen, Orem, UT (US); Anton E. Bowden, Lindon, UT (US)

(73) Assignee: Brigham Young University, Provo, UT (US)

( * ) Notice: Subject to any disclaimer, the term of this patent is extended or adjusted under 35 U.S.C. 154(b) by 71 days.

(21) Appl. No.: 15/801,317

(22) Filed: Nov. 1, 2017

(65) Prior Publication Data

US 2018/0318467 A1    Nov. 8, 2018

Related U.S. Application Data

(60) Provisional application No. 62/415,997, filed on Nov. 1, 2016.

(51) Int. Cl.
*B32B 3/00* (2006.01)
*A61L 27/50* (2006.01)
(Continued)

(52) U.S. Cl.
CPC .............. *A61L 27/50* (2013.01); *A61B 17/00* (2013.01); *A61L 27/047* (2013.01); *A61L 27/08* (2013.01); *A61L 27/303* (2013.01); *A61L 31/022* (2013.01); *A61L 31/024* (2013.01); *A61L 31/084* (2013.01); *A61L 31/14* (2013.01); *C01B 32/16* (2017.08); *C01B 32/168* (2017.08); *C09D 1/00* (2013.01); *A61B 2017/00889* (2013.01);
(Continued)

(58) Field of Classification Search
CPC ........ A61L 27/08; A61L 27/50; A61L 27/047; A61L 27/303; A61L 31/022; A61L 31/024; A61L 31/084; A61L 31/14; A61L 2420/02; C01B 32/16; C01B 32/158; C01B 2202/36
See application file for complete search history.

(56) References Cited

U.S. PATENT DOCUMENTS 6,361,861 B2    3/2002    Gao et al.
9,271,853 B2    3/2016    Skousen et al.
(Continued)

FOREIGN PATENT DOCUMENTS

JP    2001048512 A    2/2001
JP    2005001105 A    1/2005
(Continued)

OTHER PUBLICATIONS

Kang et al.; "Single-Walled Carbon Nanotubes Exhibit Strong Antimicrobial Activity;" Langmuir; (Jul. 21, 2007); pp. 8670-8673; vol. 23, No. 17; <doi: 10.1021/la701067r >.
(Continued)

*Primary Examiner* — Elizabeth E Mulvaney
(74) *Attorney, Agent, or Firm* — Thorpe North & Western, LLP

(57) ABSTRACT

Superhydrophobic materials are disclosed and described, along with devices, surfaces, and associated methods. Such materials can be coated onto device surfaces, system surfaces, structures, and the like.

22 Claims, 20 Drawing Sheets

(51) Int. Cl.
*A61L 27/30* (2006.01)
*A61L 27/04* (2006.01)
*A61L 31/02* (2006.01)
*A61L 31/08* (2006.01)
*A61L 31/14* (2006.01)
*C09D 1/00* (2006.01)
*C01B 32/168* (2017.01)
*C01B 32/16* (2017.01)
*A61B 17/00* (2006.01)
*A61L 27/08* (2006.01)
*B82Y 40/00* (2011.01)
*B82Y 5/00* (2011.01)
*B82Y 30/00* (2011.01)

(52) U.S. Cl.
CPC ............... *A61B 2017/00938* (2013.01); *A61L 2300/606* (2013.01); *A61L 2420/02* (2013.01); *B82Y 5/00* (2013.01); *B82Y 30/00* (2013.01); *B82Y 40/00* (2013.01); *C01B 2202/36* (2013.01)

(56) References Cited

U.S. PATENT DOCUMENTS

| | | | |
|---|---|---|---|
| 2004/0111141 | A1 | 6/2004 | Brabec et al. |
| 2005/0038498 | A1 | 2/2005 | Dubrow et al. |
| 2005/0260355 | A1 | 11/2005 | Weber et al. |
| 2006/0093642 | A1 | 5/2006 | Ranade |
| 2009/0196909 | A1 | 8/2009 | Cooper et al. |
| 2010/0098741 | A1 | 4/2010 | Ranade |
| 2010/0255447 | A1 | 10/2010 | Biris et al. |
| 2011/0159273 | A1 | 6/2011 | Lukowski et al. |
| 2012/0019122 | A1 | 1/2012 | Misra et al. |
| 2012/0060826 | A1 | 3/2012 | Weisenberger |
| 2012/0149003 | A1 | 6/2012 | Fan et al. |
| 2013/0285160 | A1 | 10/2013 | Davis et al. |
| 2014/0094900 | A1 | 4/2014 | Bowden et al. |
| 2015/0329362 | A1* | 11/2015 | Aria ............... B82Y 30/00 428/195.1 |

FOREIGN PATENT DOCUMENTS

| | | |
|---|---|---|
| JP | 2005049334 A | 2/2005 |
| JP | 2006069848 A | 3/2006 |
| JP | 2007027087 A | 2/2007 |
| JP | 2008/179513 A | 8/2008 |
| JP | 2009541198 A | 11/2009 |
| KR | 2013/0133700 A | 12/2013 |
| WO | WO 2013007354 A1 | 1/2013 |
| WO | WO 2013/156595 A1 | 10/2013 |
| WO | WO 2008000045 A1 | 12/2013 |
| WO | WO 2016/069811 A2 | 5/2016 |

OTHER PUBLICATIONS

Tiraferri et al.; "Covalent Binding of Single-Walled Carbon Nanotubes to Polyamide Membranes for Antimicrobial Surface Properties;" Applied Materials & Interfaces; (Jun. 30, 2011); pp. 2869-2877; vol. 3, No. 8; <doi: 10.1021/am200536p >.

Hasan et al.; "Selective Bactericidal Activity of Nanopatterned Superhydrophobic Cicada *Psaltoda claripennis* Wing Surfaces"; Applied Microbiology and Biotechnology; (Oct. 2013); pp. 9257-9262; vol. 97, Issue 20; <doi: 10.1007/s00253-012-4628-5 >.

Ivanova et al.; "Bactericidal Activity of Black Silicon"; Nature Communications; (Nov. 26, 2013); 7 pages; vol. 4, Article No. 2838; <doi: 10.1038/ncomms3838>.

Narayan et al.; "Structural and Biological Properties of Carbon Nanotube Composite Films"; Materials Science and Engineering: B; (Nov. 20, 2005); pp. 123-129; vol. 123, Issue 2; <doi: 10.1016/j.mseb.2005.07.007 >.

Aria et al.; "Dry Oxidation and Vacuum Annealing Treatments for Tuning the Wetting Properties of Carbon Nanotube Arrays"; Journal of Visualized Experiments; (Apr. 2013); 9 pages; Video Article, vol. 74, No. e50378; <doi: 10.3791/50378 >.

Esplin et al.; Super-Hydrophobic and Anti-Microbial Surfaces for Medical Instrument Application [Poster Presentation]; In: BME West Conference; (Jan. 20, 2017); Brigham Young University, Provo, Utah.

Li et al.; "Self-Assembly of Graphene on Carbon Nanotube Surfaces"; Scientific Reports; (Aug. 5, 2013); 4 pages; vol. 3, Issue 2353; <doi: 10.1038/srep02353 >.

Wang et al.; "Reversible transformation of hydrophobicity and hydrophilicity of aligned carbon nanotube arrays and buckypapers by dry processes"; Carbon; (2010); pp. 868-875; vol. 48, Issue 3; Elsevier; <doi: 10.1016/j.carbon.2009.10.041 >.

International Search Report dated Feb. 26, 2019, in International Application No. PCT/US2018/048951, filed Aug. 30, 2018; 6 pages.

Hutchison et al.; "Carbon Nanotubes as a Framework for High Aspect Ratio MEMS Fabrication;" Journal of Microelectromechanical Systems; (Feb. 2010); pp. 75-82; vol. 19, Issue 1; <doi: 10.1109/JMEMS.2009.2035639 >.

The American Heritage® Dictionary of the English Language; "Tube;" [entry]; (2019); 2 pages; Fifth Edition; [retrieved Sep. 21, 2019]; Retrieved from <URL:https://www.ahdictionary.com/work/search.html?q=tube>.

* cited by examiner

Low Cl-CNT

Medium Cl-CNT

SUPER-HYDROPHOBIC MATERIALS AND ASSOCIATED DEVICES, SYSTEMS, AND METHODS

PRIORITY INFORMATION

This application claims the benefit of U.S. Provisional Patent Application Ser. No. 62/415,997, filed Nov. 1, 2016, which is incorporated herein by reference in its entirety.

BACKGROUND

Microorganisms, including various types of bacteria, can pose a variety of health risks to both humans and animals. For example, in excess of 2 million people per year in the United States become infected with bacteria that are resistant to antibiotics. Antibiotic resistance can lead to an increase in healthcare costs, increased mortality in adults, children, and infants, and is an ever-increasing problem. One line of defense against bacterial infections in general includes careful hand washing, cleaning surfaces where bacterial can reside, and the like. Such measures, however, can be difficult to implement due to inconsistency in cleaning, as well as individual choice regarding had washing.

Further, surfaces of objects that retain fluids can harbor, not only a greater number of a given microorganism, but can also provide an environment for a wider diversity of microorganisms. Additionally, such fluid environments can concentrate biological materials usable as energy sources by microorganisms, thus further accelerating the growth of potentially harmful species.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

DESCRIPTION OF EXAMPLE EMBODIMENTS

Figure 1:
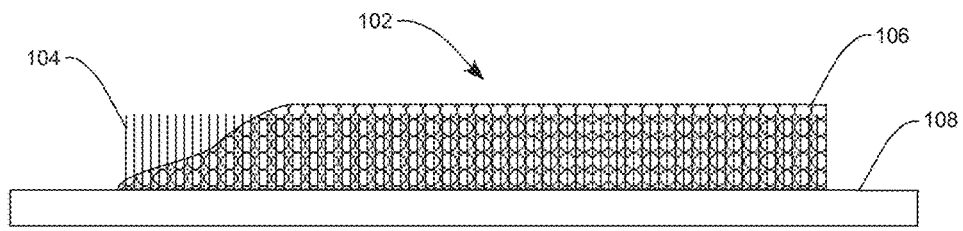
FIG. 1 illustrates a cross-sectional view of a simplified embodiment of a superhydrophobic surface according to the current technology.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence. Although the following detailed description contains many specifics for the purpose of illustration, a person of ordinary skill in the art will appreciate that many variations and alterations to the following details can be made and are considered to be included herein.

Furthermore, the described features, structures, or characteristics can be combined in any suitable manner in one or more embodiments. In the following description, numerous specific details are provided, such as examples of layouts, distances, network examples, etc., to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other methods, components, layouts, etc. In other instances, well-known structures, materials, or operations may not be shown or described in detail to avoid obscuring aspects of the disclosure.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device which is more likely to have write errors to it than other regions in the same memory device. A number of factors can cause such increased risk, including location, fabrication process, number of program pulses applied to the region, etc.

As used herein, "coupled" refers to a relationship between elements that can be, for example, physical, chemical, electrical, communicative, or the like, and includes relationships of either direct or indirect connection or attachment. Any number of items can be coupled, such as materials, components, structures, layers, devices, objects, etc.

As used herein, "directly coupled" refers to a relationship between elements that can be, for example, physical, chemical, electrical, communicative, or the like, and includes relationships where the elements have at least one point of direct physical contact or otherwise touch one another. For example, when one layer of material is deposited on or against another layer of material, the layers can be said to be directly coupled.

Objects or structures described herein as being "adjacent to" each other may be in physical contact with each other, in close proximity to each other, or in the same general region or area as each other, as appropriate for the context in which the phrase is used.

EXAMPLE EMBODIMENTS

An initial overview of example embodiments is provided below, and specific embodiments are then described in further detail. This initial summary is intended to aid readers in understanding the technological concepts more quickly, but is not intended to identify key or essential features thereof, nor is it intended to limit the scope of the claimed subject matter.

In general, microbial infections can pose many problems in healthcare, sanitation, personal well-being, and the like. One hurdle to reducing the incidence of many problematic infections across a population relates to that fact that many harmful bacteria can grow on a diverse array of surfaces. Further, the ability to multiply quickly also allows more resilient bacterial strains to proliferate despite the widespread use of antibiotics, and as a result, antibiotic resistance is increasing. This problem is compounded by surfaces that retain even small amounts of fluids, as they can harbor, not only a greater number of a given microorganism, but can also provide an environment for a wider diversity of microorganisms. Additionally, such fluid environments can concentrate biological materials usable as energy sources by microorganisms, thus further accelerating the growth of potentially harmful species. Numerous surfaces are frequently touched by many individuals throughout a day, thus potentially spreading harmful microbes such as bacteria further throughout a population. Examples of commonly touched surfaces can include, without limitation, doorknobs, soap dispensers, crosswalk buttons, handrails, support rails, phones, keyboards, computer mice, touchscreens, mobile phones, and the like, including many other commonly shared devices.

The present disclosure relates to superhydrophobic materials, surfaces, devices, etc., including methods of making such. The inventors have discovered that certain configurations of carbon nanotubes (CNTs) in a CNT layer, when infiltrated with an infiltrant material and subsequently pyrolyzed, create a superhydrophobic surface that is durable. Additionally, in some examples such superhydrophobic materials can be structurally configured to be microbially-resistant. Such coating materials can provide significant benefits for several industries, such as, for example, the medical device industry where bacterial infection and transfer is of great concern. It is noted that the term "microbe" can include any microscopic organism, whether single or multicellular. Common example microbes can include any number of bacterial species. As such, the term "bacteria" and "microbe" can be used interchangeably for convenience, with the understanding that in some cases the term "microbe" includes a broader list of possible species.

Superhydrophobic surfaces are extremely difficult to wet, and generally have a contact angle that is greater than or equal to 150 degrees. A droplet of liquid, such as water, for example, contacting a superhydrophobic surface will generally fully rebound, similar to a rubber ball. For the purposes of the present disclosure, contact angle is measured through a 0.05 mL droplet of water at the point where the water-vapor interface of the water meets a surface, such as a superhydrophobic surface. The measurement is taken at room temperature, 23 C.

In one example embodiment, a superhydrophobic composition is provided, comprising a pyrolyzed carbon-infiltrated (C-I) carbon nanotube (CNT) layer having a contact angle greater than or equal to 150 degrees for a 0.05 mL droplet of water at room temperature. The pyrolyzed C-I CNT layer is comprised of a layer of CNTs and a carbon infiltrant material infiltrated into the layer of CNTs to form a C-I CNT layer. FIG. 1 shows an oversimplified diagram of a pyrolyzed C-I CNT layer 102 including a layer of CNTs 104 and carbon infiltrant material 106 infiltrated into the layer of CNTs 104. In some examples the carbon infiltrant material 106 is infiltrated into and around the CNTs 106. FIG. 1 additionally shows a support substrate 108, upon which the pyrolyzed C-I CNT layer 102 is supported. In some cases, the CNTs 104 can be deposited on the support substrate 108 by growing CNTs from the support substrate as shown, thus forming a "forest" of CNTs extending outwardly from the support substrate. In other cases, CNTs can be grown separately from the support substrate and subsequently deposited thereon, either prior to infiltration or with an infiltrant material.

Figure 2:
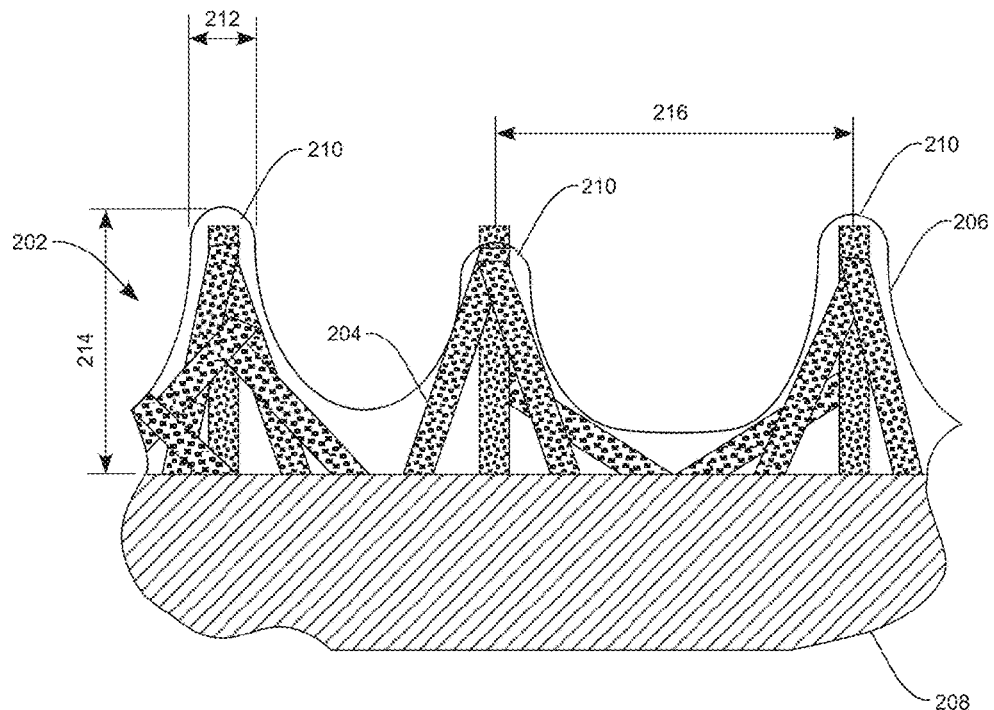
FIG. 2 illustrates a cross-sectional view of a simplified embodiment of a superhydrophobic surface according to the current technology.

In one example, FIG. 2 shows an oversimplified diagram of a pyrolyzed C-I CNT layer 202, including CNTs 204 grown from a support substrate 208 and carbon infiltrant material 206 infiltrated into and around the CNTs 204. The infiltration of the carbon material 206 can create a topological pattern of surface features 210, that in some cases can be microbially-resistant, or in other words, the infiltration of the CNTs 204 by the infiltrant material can form a microbially-resistant topological pattern of surface features 210. It is noted that a surface feature 210 can include a single CNT or multiple CNTs.

The surface features 210 have an average diameter, such as shown at 212, and an average height as shown at 214. Additionally, high-point-to-high-point average distance, such as shown at 216, can be maintained between individual surface features. It is noted that, given the infiltration process, in some cases a large number of variations in diameter, height, and distances between surface features are possible. Accordingly, while there may be a high level of uniformity between diameters, heights, and/or high-point-to-high-point distances in some embodiments, other embodiments may be more non-uniform. Example ranges for surface feature diameters, heights, and high-point-to-high-point distances are provided as a generalized description to demonstrate potential topological pattern parameters; however, it is to be understood that those skilled in the art are capable of varying pattern parameters and testing for superhydrophobicity and/or microbial growth, once in possession of the present disclosure. It is again emphasized that FIGS. 1 and 2 are overly simplified drawings for purposes of illustration only, and should not be interpreted to literally define an embodiment of the current technology.

The presently disclosed technology can be used on a variety of structures, surfaces, devices, and the like. Non-limiting examples can include various medical devices, electronic devices commonly touched surfaces, and the like, including any surface where superhydrophobicity is desired. For example, in one aspect pyrolyzed C-I CNT layers can be applied to a medical device, structure, system, etc. Such can include any surface where superhydrophobicity and/or reduced microbial growth is desired, whether inserted into a biological environment, part of a device or system in a medical environment, a diagnostic tool, a reusable item, a surface in a medical environment, or the like. Non-limiting examples can include surgical implements or instruments, implantable devices, insertable devices, diagnostic devices, prosthetic devices, medical instruments, surgical or emergency room surfaces, and the like, as well as any other surface where microbes can grow and be spread from. Other specific non-limiting examples can include scalpels, scissors, drill bits, rasps, trocars, rongeurs, graspers, claimps, retractors, distractors, dilators, suction tips, tubes, staples and staplers, staple removers, needles, scopes, measurement devices, carriers and applicators, stents, pins, screws, plates, rods, valves, orthopedic implants, cochlear implants, pacemakers, catheters, sensors and monitors, bite blocks, and the like.

In another aspect, the microbially-resistant layer can be applied to an electronic device, system, or other electronically-related surface. Non-limiting examples can include mobile phones, laptops, keyboards, mice, computer terminals, tablets, watches, touch screens, game controllers, and the like. Non-limiting examples of other devices and surfaces that may be of concern can include doorknobs, soap dispensers, crosswalk buttons, handrails, support rails, countertops, food preparation and serving items, and the like.

In one embodiment, the current technology can employ a CNT layer coupled to a support substrate. As will be recognized in the art, there are a variety of methods to manufacture CNTs, such as arc discharge, laser ablation, plasma torch, high-pressure carbon monoxide disproportionation (HiPCO), chemical vapor deposition (CVD), water-assisted CVD, and the like. The present scope is not limited by the technique of preparing the CNTs, or by the particular technique of infiltration. In one non-limiting example using MEMS manufacturing processes, a mask can be made with a detailed 2-dimensional geometry. The CNTs can be grown vertically extruding the 2-dimensional geometry into a 3-dimensional CNT forest. Thus, in one aspect, the CNT layer of the current technology can be grown from the support substrate, either by this or another technology, with or without using a mask. In another aspect, the CNTs can be grown or otherwise produced on a separate substrate, removed, and subsequently deposited on the support substrate in a molded fashion to form the CNT layer.

The CNT layer can be formed or otherwise deposited onto the support substrate, and the infiltrant material can be infiltrated into the CNT layer to form a topological pattern of surface features that is microbially-resistant. The CNT layer can be applied to the support substrate in a pattern that assists in the formation of the topological pattern as described, or the CNTs can be applied irrespective of the final topological pattern. Various infiltrant materials can be utilized, including, without limitation, carbon, pyrolytic carbon, carbon graphite, various polymers, or any other hydrophobic material capable of infiltration and pyrolysis.

Following infiltrating with the infiltrant material, the resulting layer can be microbially-resistant, independent of chemical composition. For example, the microbially-resistant topological pattern of surface features can be configured to oppose microbial or bacterial contact with the support substrate. Thus, the bacteria can be restricted at the termini of a group of surface features and prevented from accessing and adhering to the support surface to replicate and grow. Furthermore, the surface features themselves, or combinations thereof, can be configured or spaced so as not to provide an adequate growth surface for the bacterial cell. In other words, the topological pattern of surface features has a surface feature density that is sufficient to limit microbial contact with the support substrate and insufficient for the surface features themselves to act as a microbial growth substrate. As such, infiltrated carbon nanotube layer does not include an adequate surface that promotes microbial or bacterial growth.

Accordingly, the microbially-resistant topological pattern of surface features can be configured to reduce bacterial growth on the support substrate. In one embodiment, the microbially-resistant topological pattern of surface features can provide a bacteriostatic surface by preventing the bacteria from adhering to the surface and replicating. In another embodiment, the microbially-resistant topological pattern of surface features can provide a bactericidal surface. In one aspect, the surface can be bactericidal where the surface features are configured to puncture or pierce the cell wall/membrane of the bacterial cell. In another aspect, the surface can be bactericidal where the surface features are configured to tear or rupture the cell wall/membrane of the bacterial cell as its own mass bears down on the individual surface features.

In order to form the microbially-resistant topological pattern of surface features, the pattern and surface features are combined in a bacterially-resistant manner. For example, the pattern can provide a spacing between surface features that prevents or reduces access of bacterial cells to the support substrate. However, the spacing may also be sufficiently large so that the surface features themselves do not provide a growth substrate for the bacterial cell. Similarly, the surface features can have appropriate diameters and heights to accommodate the spacing between the surface features in order to restrict the bacterial cell from the support substrate and without providing a growth surface for the bacterial cell, as has been described. Thus, different combinations of densities, diameters, heights, and the like can achieve a suitable microbially-resistant topological pattern of surface features, which can be optimized for specific applications and bacterial cells.

Accordingly, the microbially-resistant topological pattern of surface features can have a variety of densities. In one aspect, the microbially-resistant topological pattern of surface features can have a density of from 1 surface feature per $\mu m^2$ to 10,000 surface features per $\mu m^2$. In another aspect, the bacterially-resistant topological pattern of surface features can have a density of from 25 surface features per $\mu m^2$ to 7300 surface features per $\mu m^2$. In another aspect, the bacterially-resistant topological pattern of surface features can have a density of from 750 surface features per $\mu m^2$ to 5000 surface features per $\mu m^2$. In yet another aspect, the surface features can have an average high-point-to-high-point spacing of from about 500 nm to about 1100 nm. In another aspect, the surface features have an average high-point-to-high-point spacing of from about 600 nm to about 1000 nm.

The surface features can have a variety of diameters. The diameter of the surface feature can be relevant for a variety of reasons. For example, if the diameter is too small, the surface feature can lack sufficient stiffness to support a bacterial cell. Thus, the surface feature can be displaced or bent in such a way as to allow the bacterial cell access to the support substrate for adhesion, growth, and replication. However, if the diameter is too large, the surface features can begin to abut one another, or they can be sufficiently large themselves, to provide a growth surface for the bacteria. Further, different infiltrant materials can impart different structural characteristics, and as such, infiltration to different diameters may be useful for different materials. In one general aspect, the surface features can have a diameter of from 10 nm to 1000 nm. In another general aspect, the surface features can have a diameter of from 50 nm to 500 nm. In another general aspect, the surface features can have a diameter of from 100 nm to 200 nm. In another general aspect, the surface features can have a diameter of from 150 nm to 300 nm. In a further general aspect, the surface features can have a diameter of from 200 nm to 250 nm.

The surface features can also have a variety of heights. The relevance of a specified height parallels that of the description of diameter to some extent. The taller a surface feature, the more it will bend, thus allowing access to the support substrate by the microorganism. Thus, in one aspect, the surface features can have a height of about 1 diameter of a bacterial cell. While bacteria can have a variety of diameters, surface features can be specifically designed for specific sized or specific ranges of bacteria. Additionally, many bacteria have a diameter ranging from 0.2 µm to 2 µm, and as such, in some aspects the heights of surface features can range from 0.2, 0.5, 1 or 2 µm to 10, 100, or 1000 µm from the support substrate surface. In another example, CNTs can be grown on the support substrate to an average height of from about 20 to about 75 microns from the support substrate surface. In another example, CNTs can be grown on the support substrate to an average height of from about 30 to about 50 microns from the support substrate surface.

As previously described, depositing a CNT layer can be performed using a variety of methods known in the art. In one aspect, the CNT layer can be grown on the support surface. In another aspect, the CNT layer can be deposited on the surface via at least one of CVD or PVD. In another aspect, the CNTs can be grown or deposited on a separate substrate and transferred or applied to the support substrate.

Suitable types of support substrates can include any type of useful material on which a the present layer can be formed. In one aspect, for example, the support substrate can include various metals, metal alloys, polymers, ceramics, semiconductors, and the like, including combinations thereof. Non-limiting examples can include iron, steel, stainless steel, nickel, aluminum, titanium, brass, bronze, zinc, and the like, including combinations thereof. Other non-limiting examples can include polyethylenes, polyvinyl chlorides, polyethylenes, polypropylenes, polystyrenes, polyamides, polyimides, acrylonitrile butadiene styrenes, polycarbonates, polyurethanes, polyetheretherketones, polyetherimides, polymethyl methacrylates, polytetrafluoroethylenes, urea-formaldehydes, furans, silicones, and the like, including combinations thereof. Yet other non-limiting examples can include silicon, quartz, glass, and the like, including combinations thereof.

In another aspect, a method of making a superhydrophobic surface is provided. Such a method can include depositing a CNT layer on a support substrate, infiltrating the CNT layer with a carbon infiltrant material to form a C-I CNT layer, and pyrolyzing the C-I CNT layer to form a pyrolyzed C-I CNT layer. The resulting superhydrophobic surface has a contact angle that is greater than or equal to 150 degrees. Pyrolyzing the C-I CNT layer can, in one example, at least partially crystallize the C-I CNT layer, and can remove deformities and impurities that reduce the hydrophobicity of the material. Contrary to the understanding in the art that pyrolyzing can degrade the quality of carbon nanotube materials, particularly for prolonged durations, the inventors have found that pyrolysis can be utilized to increase the quality of such materials, thereby increasing the superhydrophobicity thereof.

In one example, the C-I CNT layer can be pyrolyzed in an oxygen-free environment for a sufficient time at a sufficient temperature to produce the pyrolyzed C-I CNT layer having a contact angle greater than or equal to 150 degrees. It is noted that the term "oxygen-free" refers to conditions where pyrolysis can occur with negligible to no oxidation of the material being pyrolyzed. As is understood in the art, an environment completely devoid of oxygen molecules is difficult if not impossible to achieve. "Oxygen-free" examples can include, without limitation, a vacuum, various inert gasses, such as argon, for example, and the like. The duration and temperature of the pyrolysis can vary widely, depending on the equipment used in the process, the desired results, the materials being pyrolyzed, including substrates and devices, and the like. For example, the duration of the pyrolytic process can depend on the temperatures used, which can in turn depend on the specific specifications of the oven used for heating. In some cases, pyrolysis times can be longer at lower temperatures and shorter at higher temperatures, although this trend need not be followed. Regardless, those skilled in the art can readily determine sufficient/appropriate temperature and duration ranges to achieve a durable superhydrophobic material having a contact angle greater than or equal to 150 degrees. In one example, however, the sufficient temperature is greater than or equal to 150 C. In another example, the sufficient temperature is greater than or equal to 200 C, 300 C, or more. In a further example, the sufficient temperature is from 600 C to 800 C, or more. In another example, the sufficient temperature is from 200 C to the temperature limit of the furnace used. In one example, the sufficient time for pyrolysis can range from 1 minute or less to several days, or more. In one specific aspect, a C-I CNT layer can be pyrolyzed for up to 24 hours or more at 200-250 C. In another example, a C-I CNT layer can be pyrolyzed for from 1 minute to 30 minutes at 800 C.

EXAMPLES

Infiltrated Carbon Nanotubes

Carbon nanotubes were grown at 750° C. using ethylene gas as the carbon source at a flow rate of about 146 sccm. Iron layers 2-10 nm thick were used as a catalyst for nanotube growth. The samples tested for biofilm growth were grown using a 7 nm catalyst layer. Nanotube density was controlled by the thickness of the iron catalyst layer deposited before growth. The carbon nanotubes were infiltrated using ethylene gas as a carbon source (flow rate of about 214 sccm), at 900° C., for 1-60 minutes to produce carbon infiltrated carbon nanotubes (CI-CNTs).

Figure 3:
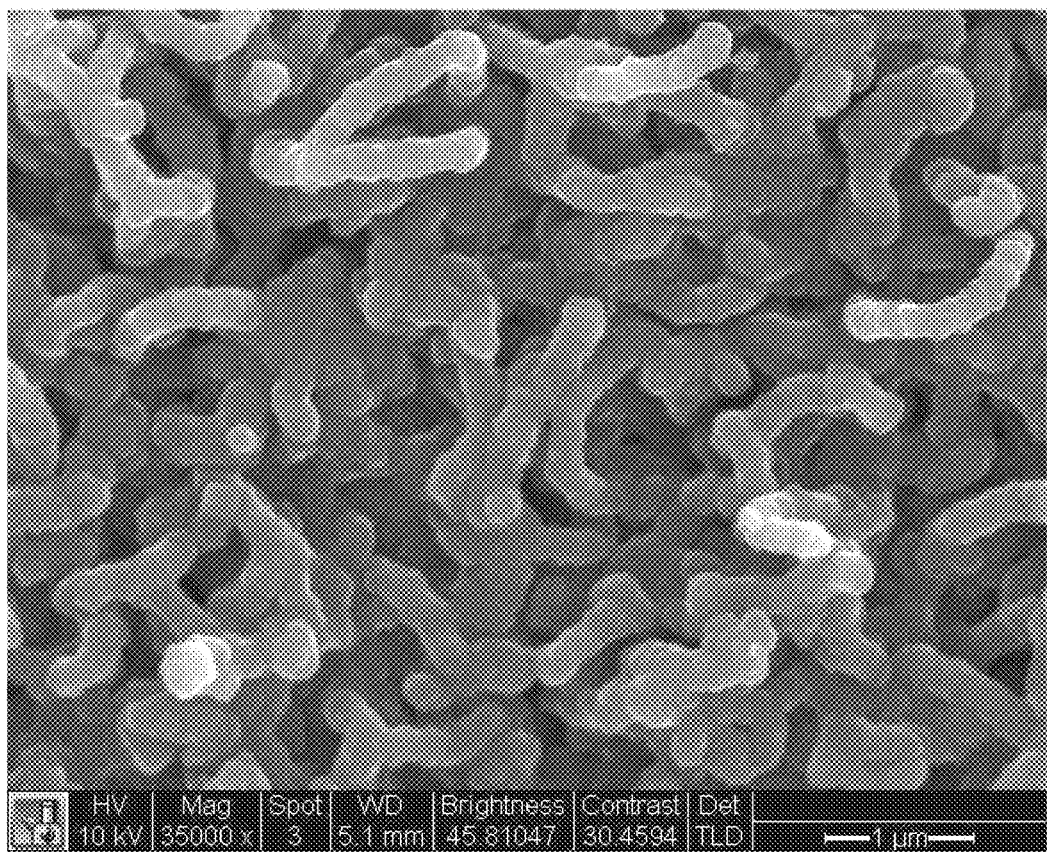
FIG. 3 illustrates a top view of one embodiment of a surface according to the current technology having a medium infiltration level.

FIG. 3 shows an image of a medium (30-minute) infiltration sample from the top. This image illustrates surface features that are about 100-200 nm in diameter, and are spaced roughly 300-500 nm apart.

Figure 4:
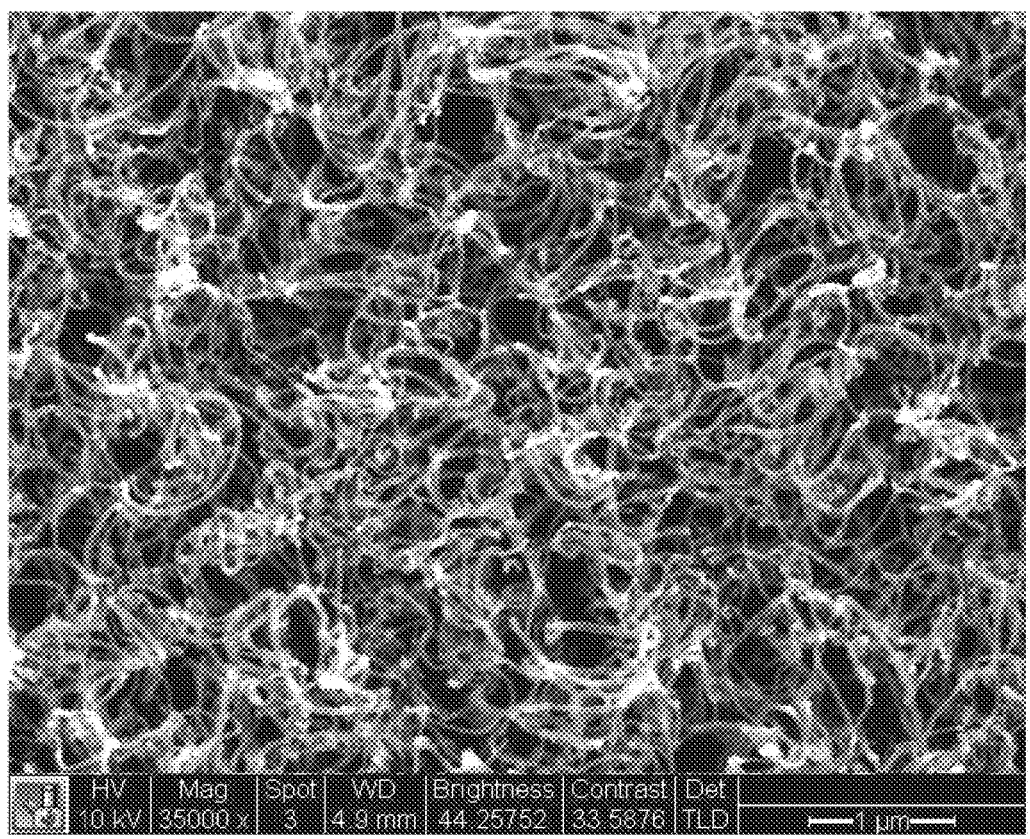
FIG. 4 illustrates a top view of one embodiment of a surface according to the current technology having a low infiltration level.

FIG. 4 shows an image of a low (3-minute) infiltration sample from the top. In this case, the pillars are about 20-50 nm in diameter.

Figure 5:
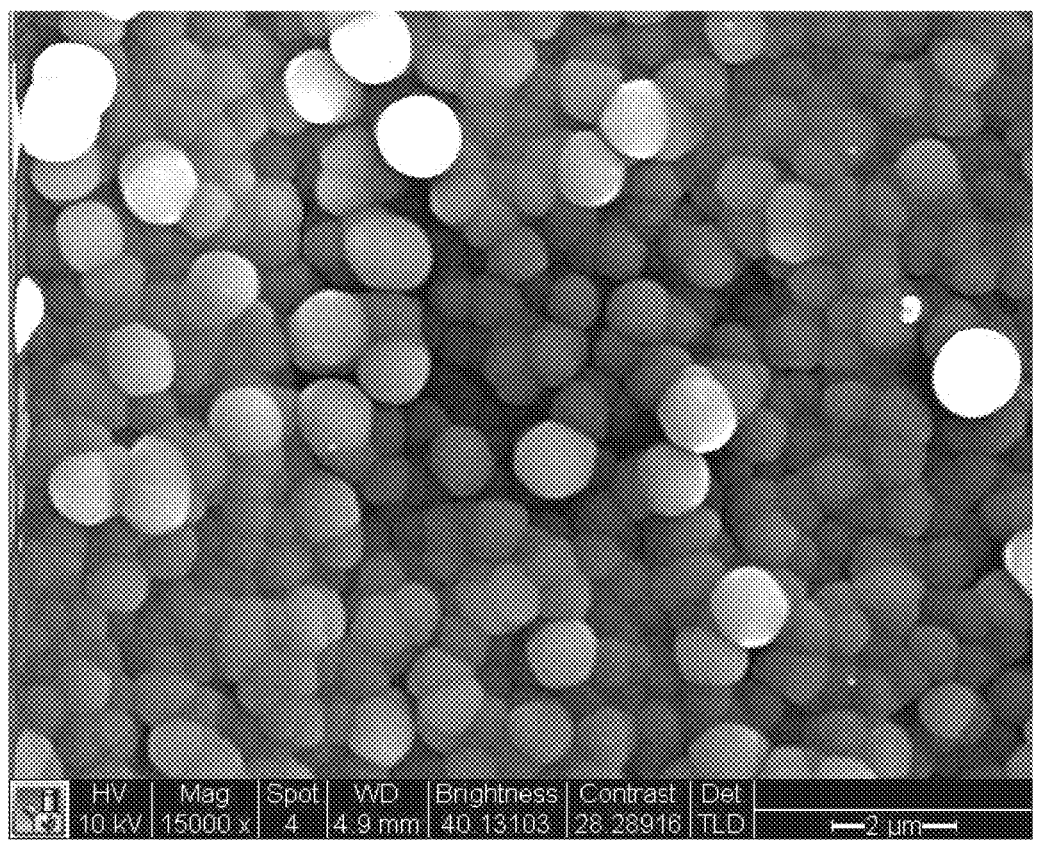
FIG. 5 illustrates a top view of one embodiment of a surface according to the current technology having a high infiltration level.

FIG. 5 shows a high (60-minute) infiltration sample from the top. In this case, the carbon nanotube layer has completely filled in, leaving abutting spherical protrusions from the surface instead of spaced surface features.

Figure 6:
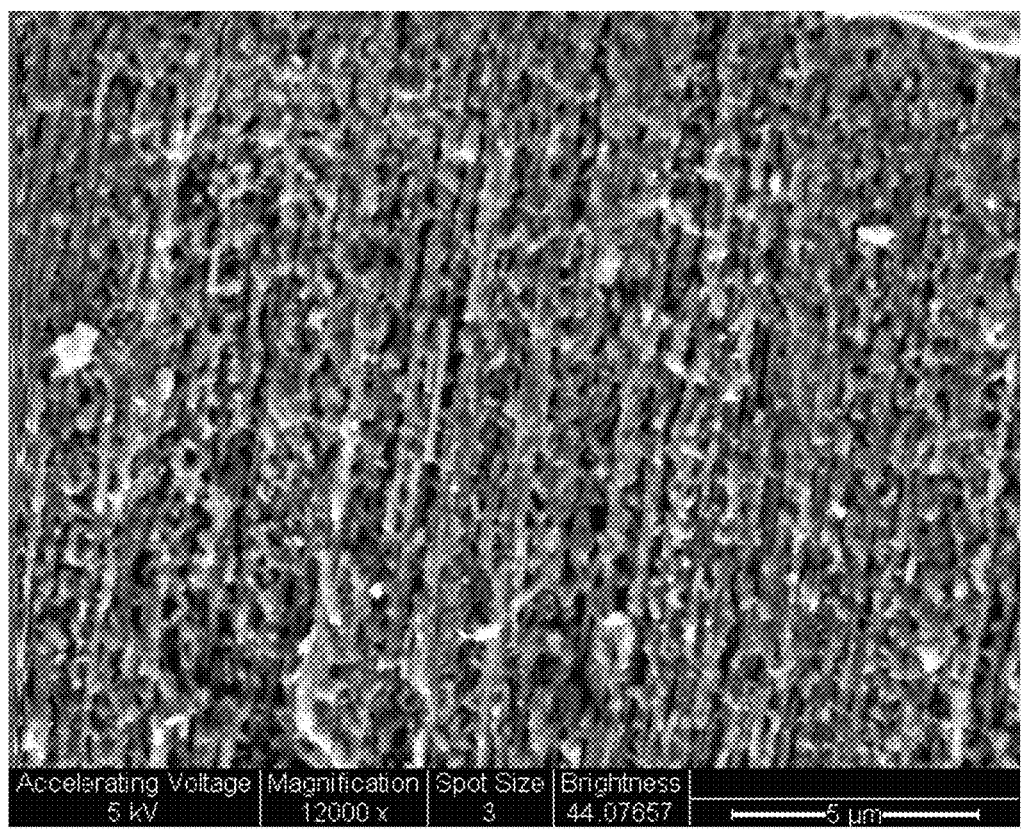
FIG. 6 illustrates a side view of one embodiment of a surface according to the current technology.

FIG. 6 shows a sample carbon nanotube forest from the side, illustrating that the infiltration material coats the whole length of the nanotubes, leaving behind voids (or pores) in the material.

Microbially Resistance of Surfaces

Figure 7:
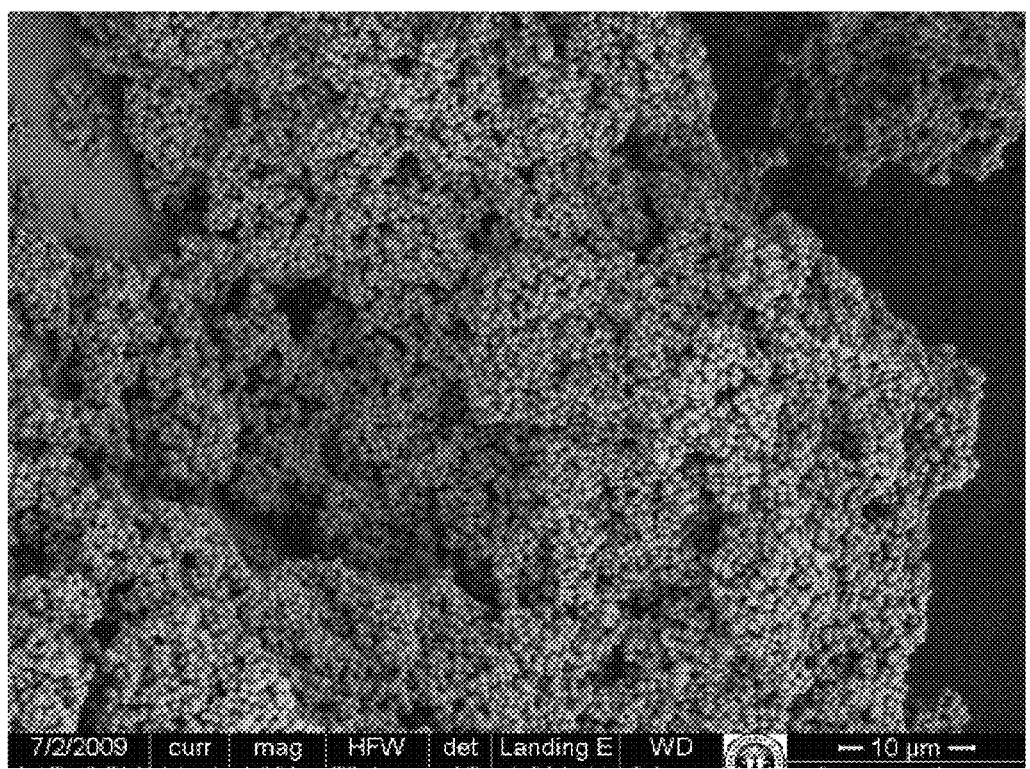
FIG. 7 illustrates a MRSA biofilm on a titanium substrate according to the current technology.
Figure 8A:
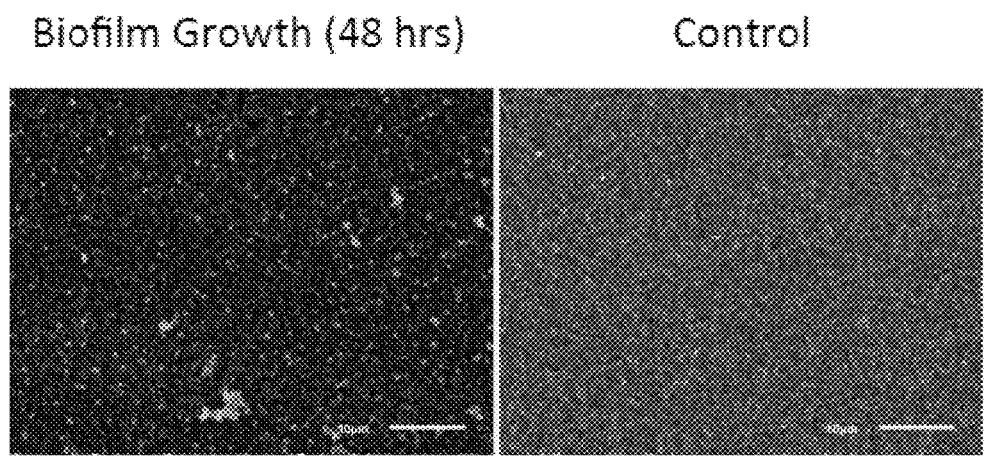
FIG. 8A illustrates a comparative test and control sample for MRSA biofilm growth according to the current technology.
Figure 8B:
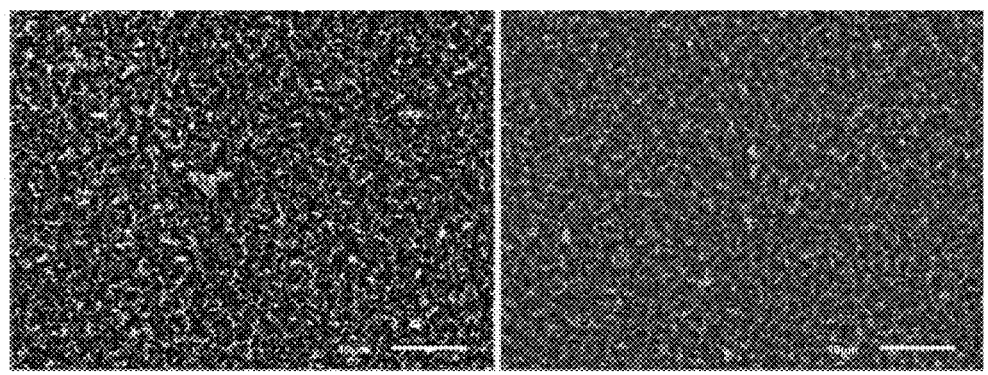
FIG. 8B illustrates a comparative test and control sample for MRSA biofilm growth according to the current technology.
Figure 8C:
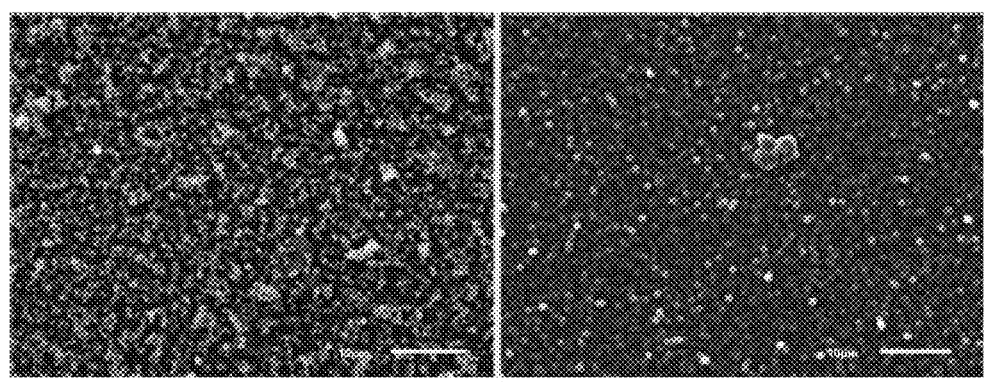
FIG. 8C illustrates a comparative test and control sample for MRSA biofilm growth according to the current technology.

MRSA biofilm testing was performed on CI-CNT surfaces to determine bacterial resistance. Three CI-CNT samples and controls were prepared at different infiltration levels: low, medium, and high, as described in Example 1 above. Each of the test samples was inoculated with MRSA bacteria, whereas the control samples were not. Subsequently, each of the samples and controls were put into an environment that would allow MRSA bacteria to flourish and create biofilms for 48 hours. Typically, biofilms are generated like those illustrated in FIG. 7. However, as can be seen in FIG. 8, there is little to no difference between test samples and control samples, despite the test samples being inoculated with MRSA bacteria and provided with an optimal growth environment for 48 hours. Thus, while there are bacterial cells on the CI-CNT surfaces, they did not replicate as anticipated under the growth conditions to produce typical biofilms, as illustrated in FIG. 7. This would indicate that the CI-CNT surfaces resist bacterial growth and replication.

Figure 9A:
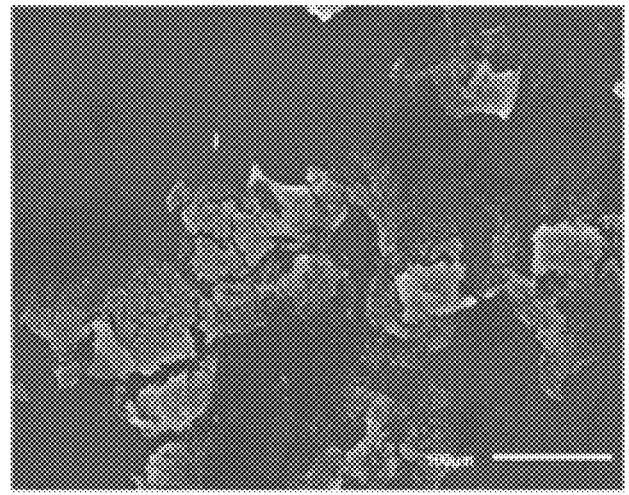
FIG. 9A illustrates a comparative test sample for MRSA biofilm growth according to the current technology.
Figure 9B:
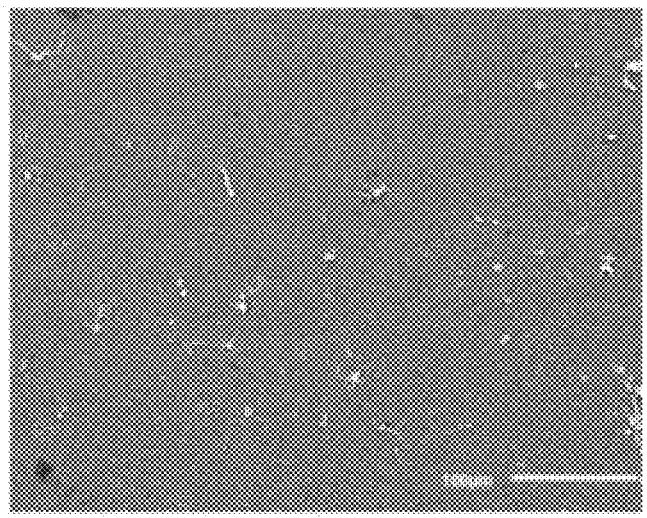
FIG. 9B illustrates a comparative test sample for MRSA biofilm growth according to the current technology.
Figure 9C:
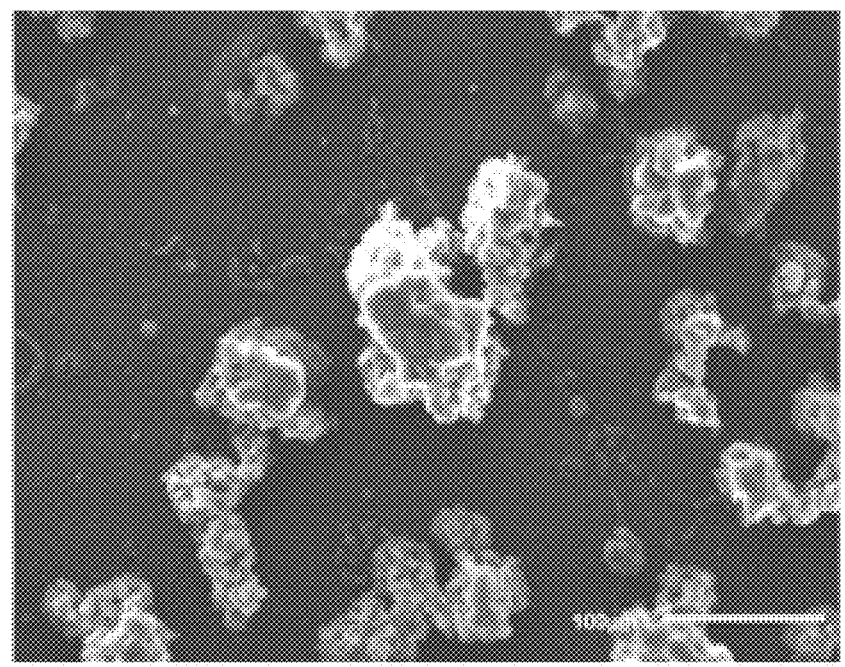
FIG. 9C illustrates a comparative test sample for MRSA biofilm growth according to the current technology.

An additional study was performed similar to the previous test with the exception that 24 samples were tested at one time. Each of the samples was placed in the same chamber for a 48-hour incubation period. Representative SEM images are illustrated by FIG. 9. There are morphological differences between the various images, but this is not uncommon for biofilms. The medium infiltration resisted the biofilm better than both the low and high infiltration samples. Further, based on the infiltration parameters described in Example 1, it was observed that a highly effective surface feature configuration can be obtained by infiltrating for about 16 minutes at 950° C.

Growing CI-CNTs on Stainless Steel

Figure 10:
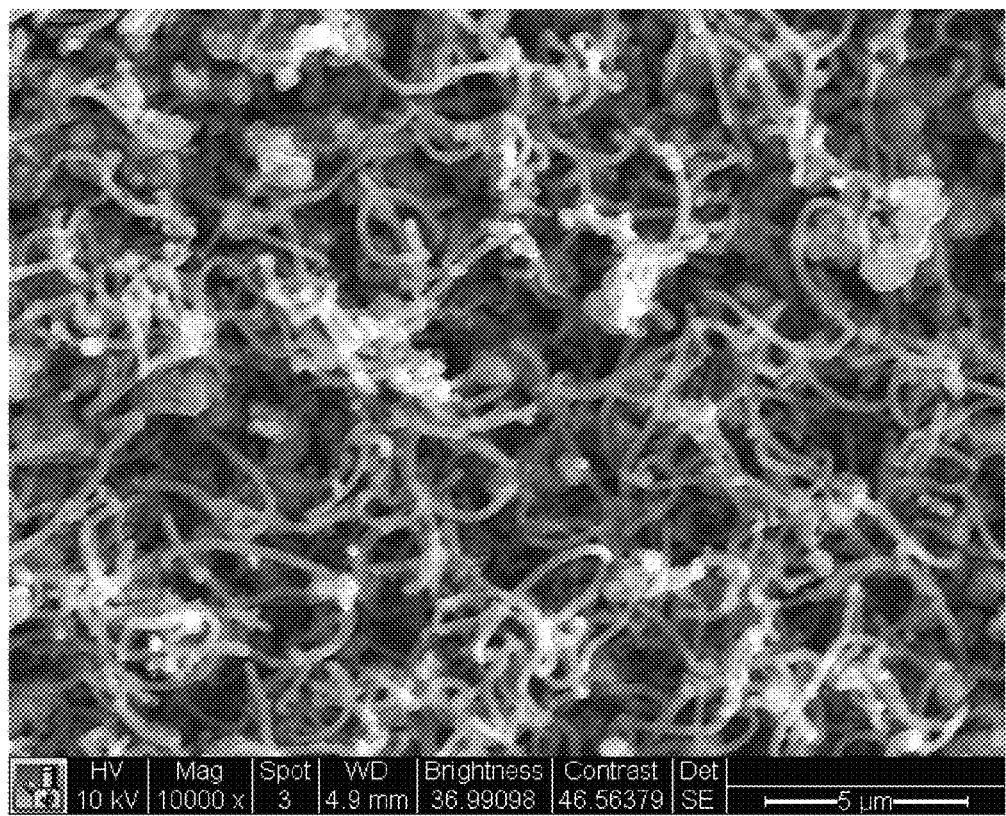
FIG. 10 illustrates a top surface of CI-CNTs grown directly onto stainless steel (SS) according to the current technology.

Iron is a catalyst for CNT growth. Accordingly, this study explored whether the iron present in stainless steel (SS) can be used as a catalyst for CNT growth. As can be seen in FIG. 10, CNTs can be grown directly on the SS surface without an external catalyst. This can dramatically simplify the manufacturing process. Also, because the catalyst is inside the substrate, the adhesion strength can be improved. This can allow for coating SS medical implants or tools with CNTs to gain the benefit of their antibacterial properties.

Though a variety of methods can be used, the current SS samples were etched in high concentration HCl for 15 minutes. The samples were then transferred into a furnace for growth and infiltration. This etching process can partially remove the chromium-oxide layer on the SS and allow for iron to be used as the catalyst during CNT growth.

Figure 11:
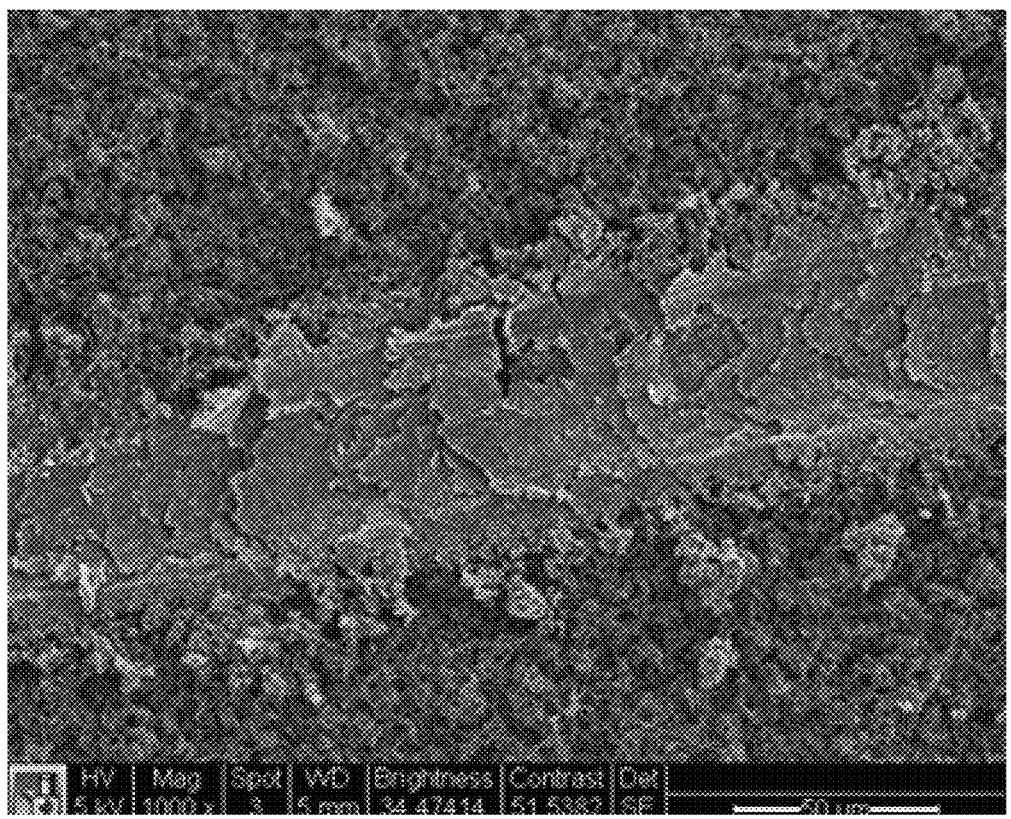
FIG. 11 illustrates CI-CNTs on SS post-scratch test according to the current technology.

The SS samples were analyzed by SEM imaging and scratch tests. The top surfaces were SEM imaged to see if they matched silicon substrate surfaces visually. As shown in FIG. 10, SS samples do match the silicon substrates having medium infiltration levels, but the samples did require a longer infiltration time. Scratch testing was performed by using sharp tweezers to scratch on the surface (FIG. 11). Generally, the adhesion for CI-CNTs on SS is polarized, such that they either adhere very well or they flake off with a minimal contact.

Figure 12:
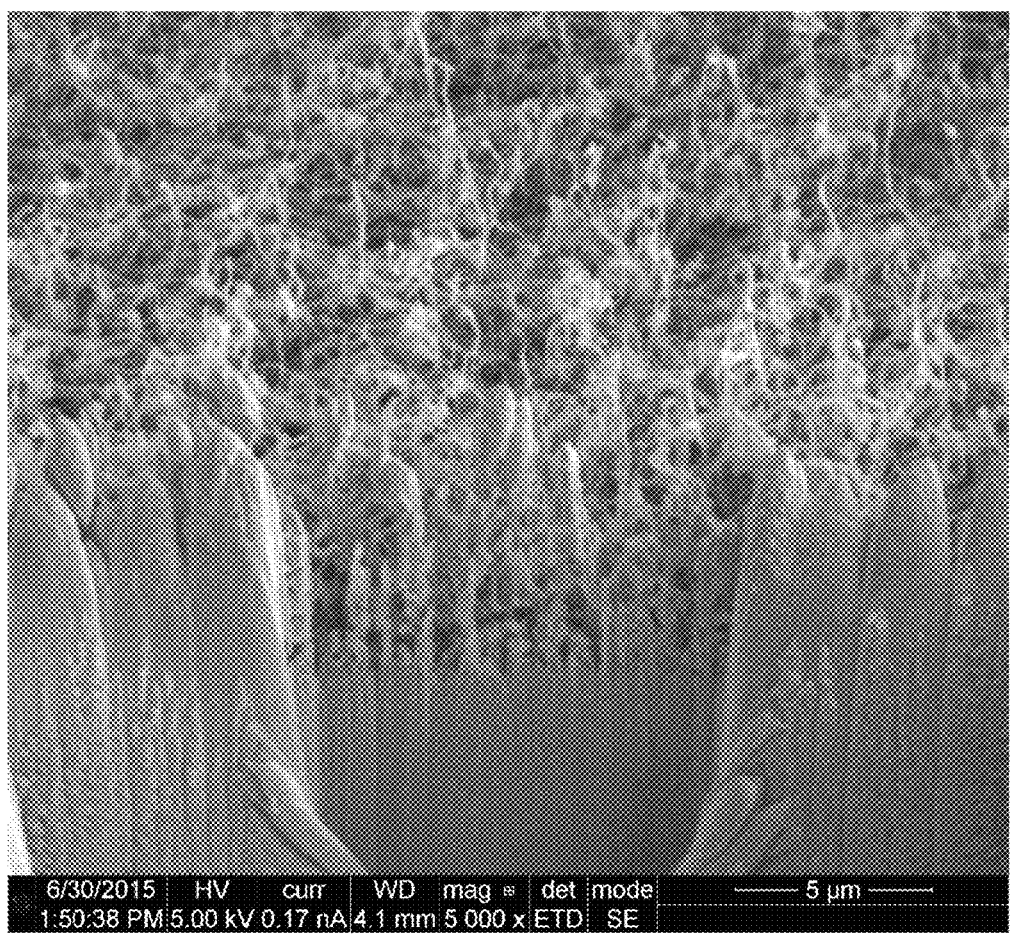
FIG. 12 illustrates a 15 second growth with a FIB (focused ion beam) cut depicting CI-CNTs having about a 4 µm height according to the current technology.

As illustrated in FIG. 12, a 15-second growth on SS can result in about a 4 μm growth height. Growth density and characteristics are generally similar to the typical silicon samples.

Growing CI-CNTS on Various Substrate Configurations

Figure 13:
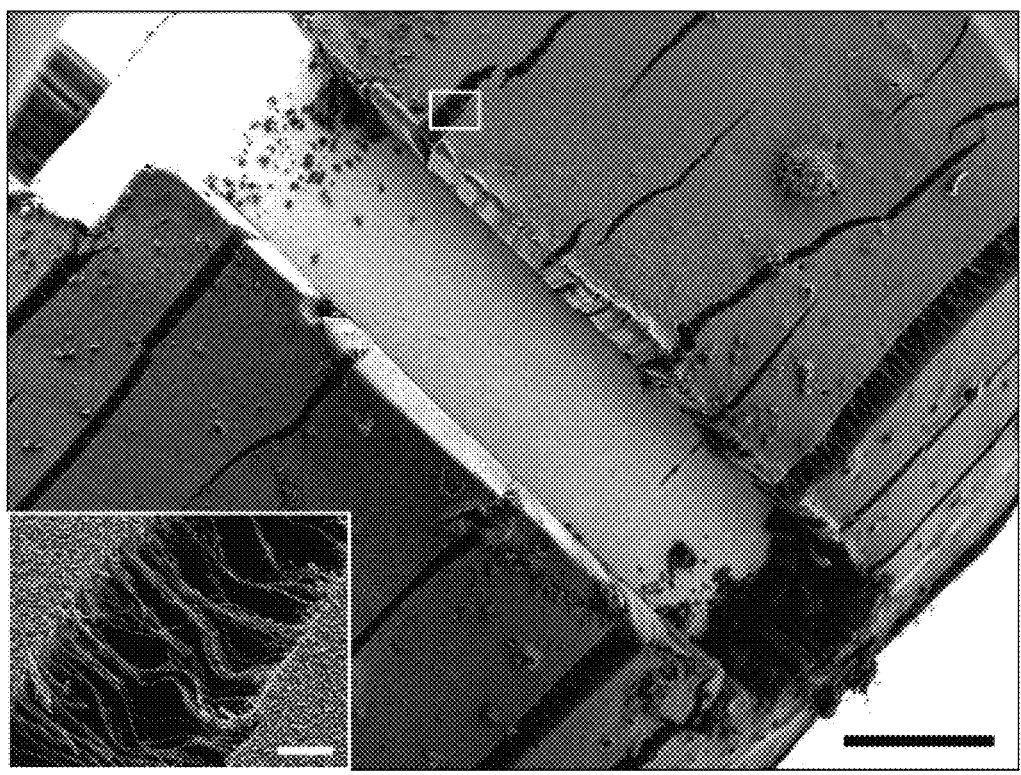
FIG. 13 illustrates a CI-CNT patterned coating on a 3 mm diameter rod according to the current technology.

One of the unique features of CI-CNTs is that they "grow," which means that they have the potential to be coated onto a variety of surface geometries. Accordingly, this study looked at the characteristics of CI-CNTs grown on various surface geometries. First, 3 mm diameter rods were coated with CI-CNTs. It was discovered that convex substrates can have problems with cracking (FIG. 13).

Figure 14:
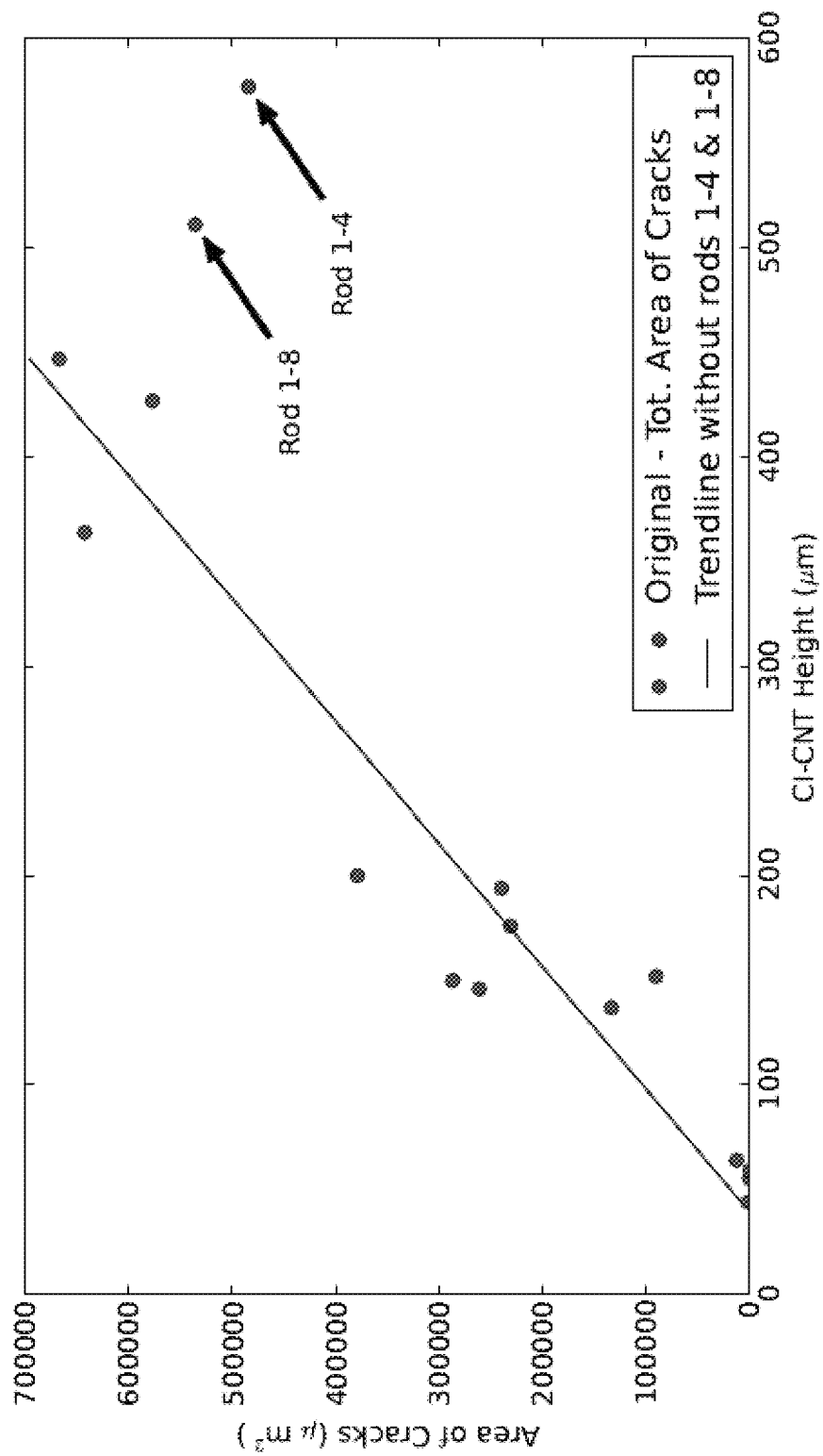
FIG. 14 is a graphical representation of the area of cracks vs. CI-CNT height according to the current technology.

In order to evaluate the cause for this cracking phenomenon, iron thickness, CNT height, infiltration level, and cooling time after growth were measured. The results indicated that iron thickness and CNT height were the primary variables that affected cracking. Increasing iron thickness decreased the area of cracks. Increasing the CI-CNT height increased the area of cracks (FIG. 14). Thus, optimization of these variables can be used to minimize, and eventually eliminate, CI-CNT cracks on concave surfaces.

Figure 15A:
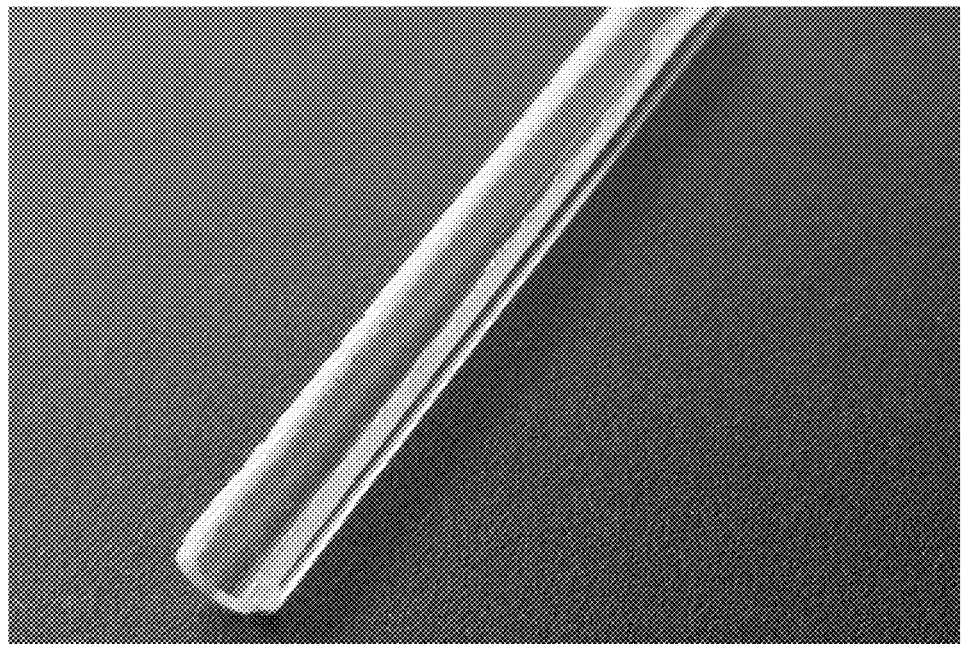
FIG. 15A illustrate a concave quartz tube substrate used in this study that was cut in half lengthwise.
Figure 15B:
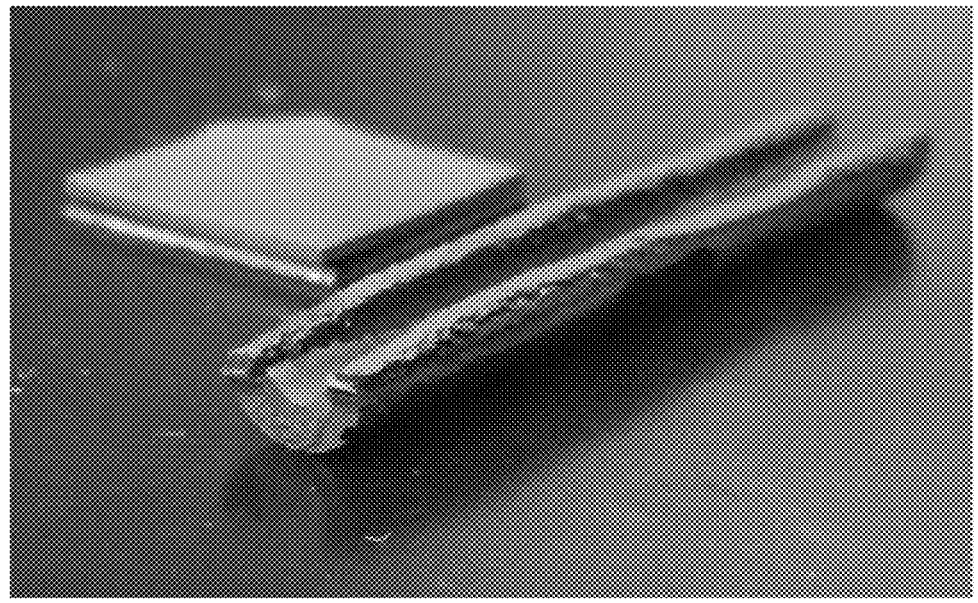
FIG. 15B illustrate a couple of concave quartz tube substrates used in this study that were cut in half lengthwise.
Figure 16:
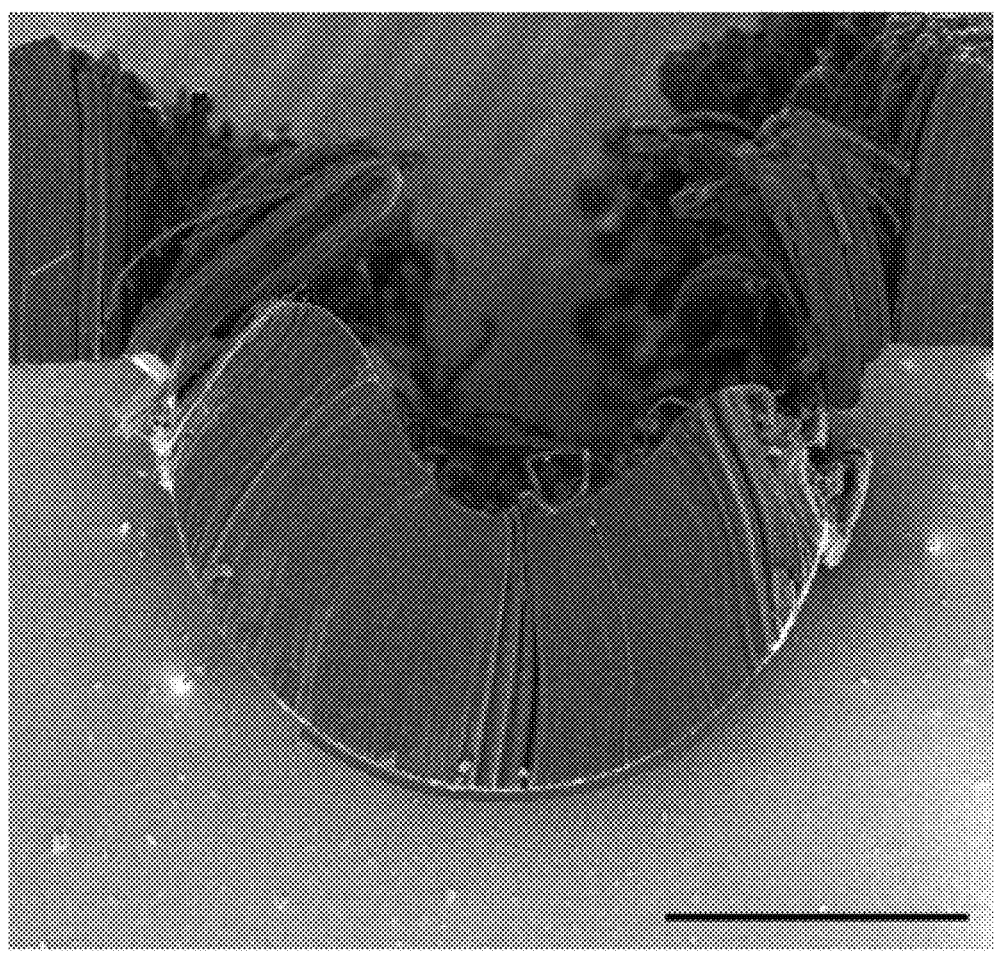
FIG. 16 illustrates a cross-sectional view of a 1 mm ID with long CI-CNT growth. Red mark shows which CI-CNTs were analyzed.
Figure 17A:
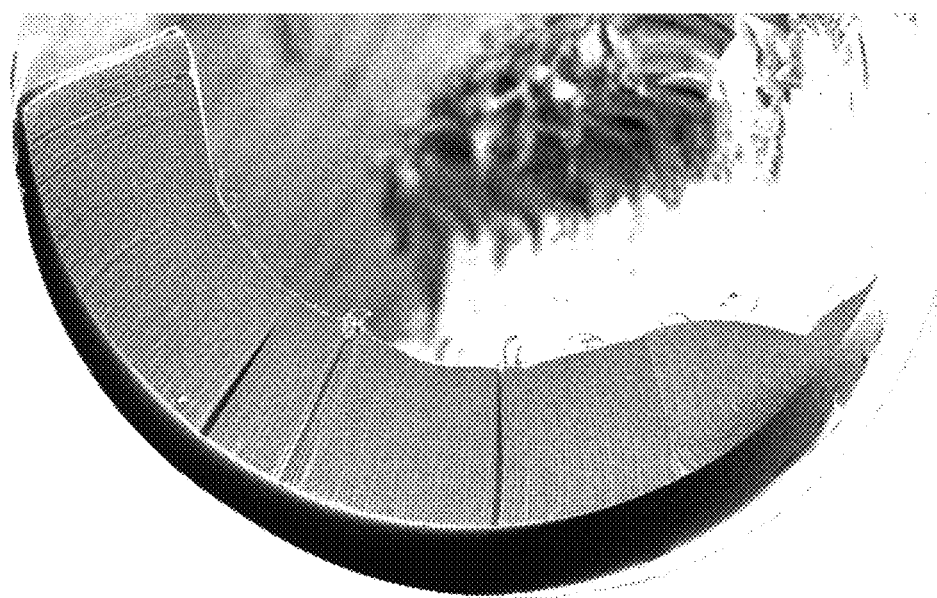
FIG. 17A shows a comparison between inner diameters (IDs) and CI-CNT growth heights for small ID, long growth, according to the current technology.
Figure 17B:
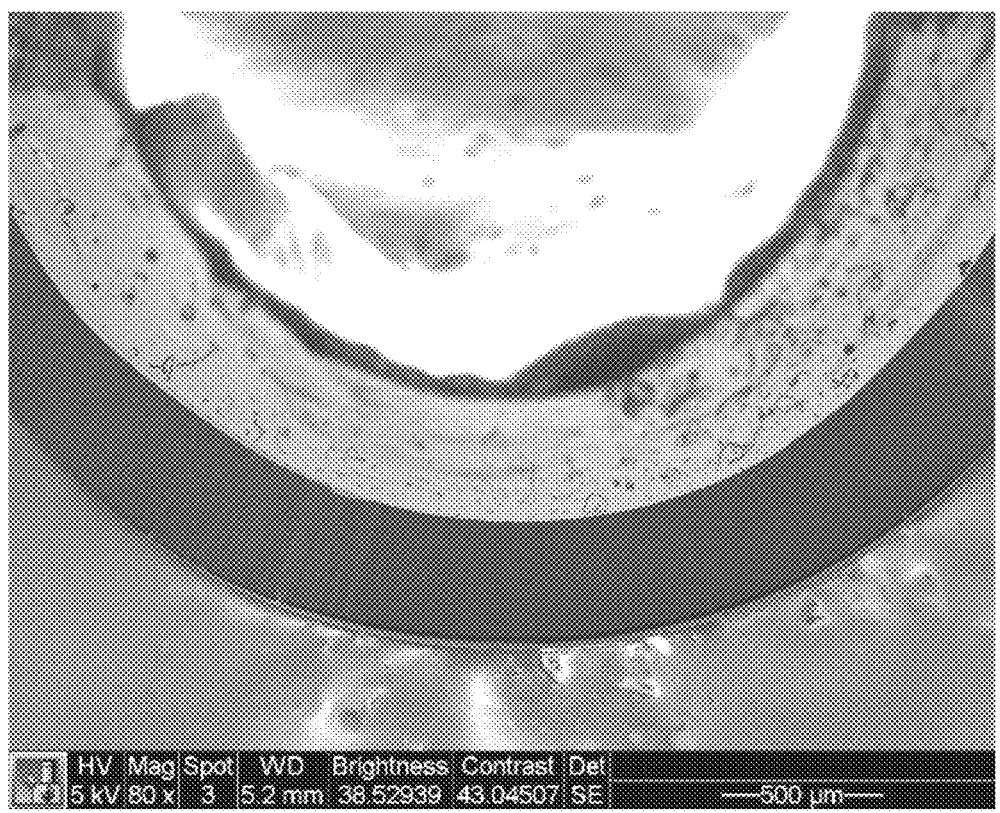
FIG. 17B shows a comparison between inner diameters (IDs) and CI-CNT growth heights for large ID, long growth, according to the current technology.
Figure 17C:
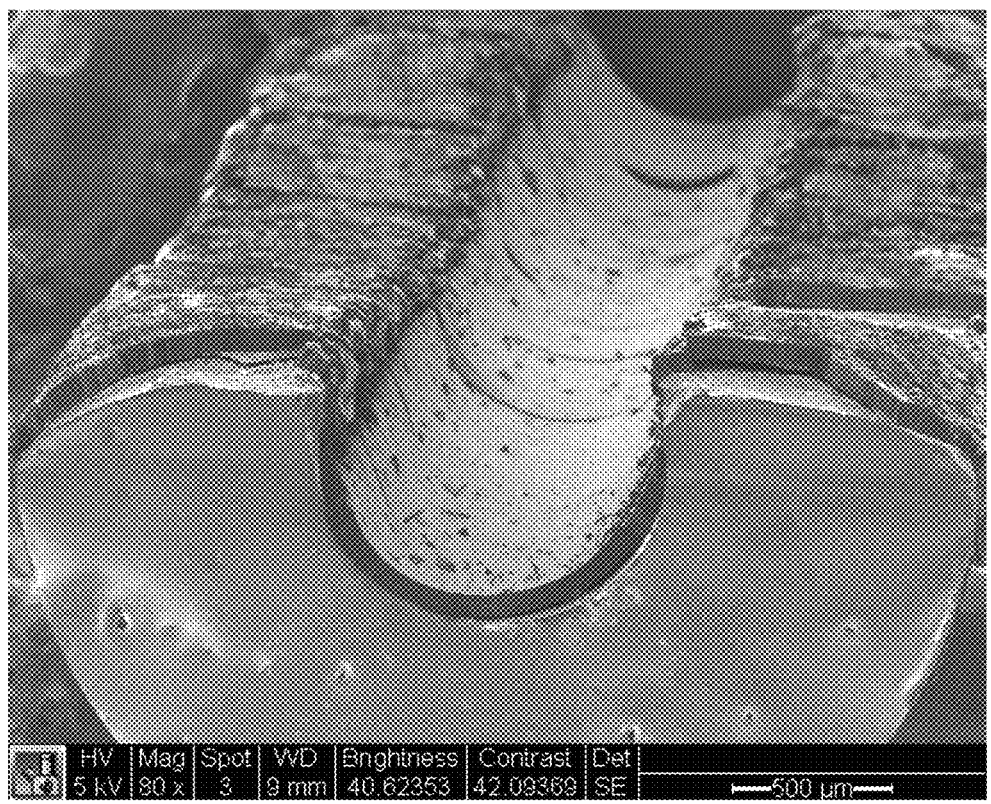
FIG. 17C shows a comparison between inner diameters (IDs) and CI-CNT growth heights for small ID, short growth, according to the current technology.
Figure 17D:
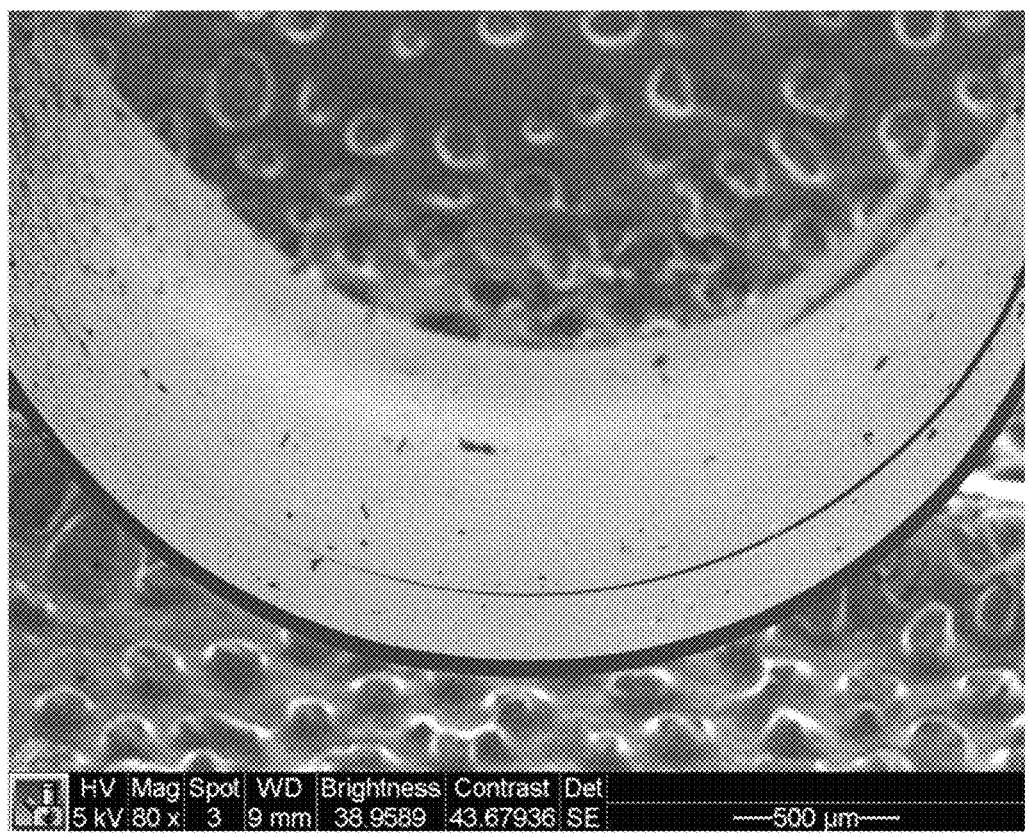
FIG. 17D shows a comparison between inner diameters (IDs) and CI-CNT growth heights for large ID, short growth, according to the current technology.

Concave substrates were also evaluated. Specifically, two variables were tested: radius of curvature and CI-CNT height. Quartz tubes were cut along the axis, and CI-CNTs were grown using the same methods as a silicon wafer substrate (FIGS. 15A-B). After the growth and infiltration, each tube was broken in half to SEM image the inside cross-section. These SEM images exposed defects in the growths such as CNT curving and inside crevices (FIG. 16) that confirm the importance of coordinating inner diameter (ID) and CI-CNT height. Examples of the SEM results can be seen in FIGS. 17A-17D. Overall, long CI-CNT growths combined better with large IDs (3-4 mm) than small IDs (1-2 mm). However, short CI-CNT growths combine well with all IDs tested. One potential drawback to the short CI-CNT growths is that they can be quite fragile. This can result partially because the CNTs do not adhere to the quartz tubing. However, this will not be an issue when they are adhered to a substrate such as stainless steel.

In one example there is provided a superhydrophobic composition, comprising a pyrolyzed carbon-infiltrated (C-I) carbon nanotube (CNT) layer having a contact angle greater than or equal to 150 degrees for a 0.05 mL droplet of water at room temperature, including a layer of CNTs and a carbon infiltrant material infiltrated into the layer of CNTs to form a C-I CNT layer.

In one example, the composition comprises a support substrate upon which the pyrolyzed C-I CNT layer is supported.

In one example composition, the layer of CNTs extends from the support substrate.

In one example composition, the layer of CNTs have been grown on the support substrate.

In one example composition, CNTs for the layer of CNTs are grown separately from, and subsequently deposited onto, the support substrate.

In one example composition, the carbon infiltrant material is infiltrated into and around CNTs of the layer of CNTs.

In one example composition, the support substrate includes a member selected from the group consisting of metals, metal alloys, polymers, ceramics, semiconductors, and combinations thereof.

In one example composition, the pyrolyzed C-I CNT layer further comprises a microbially-resistant topological pattern of surface features.

In one example composition, the topological pattern of surface features has a structural configuration that limits microbial contact.

In one example composition, the topological pattern of surface features has a surface feature density, wherein the surface feature density is sufficient to limit microbial contact and insufficient for the surface features to act as a microbial growth substrate.

In one example composition, the CNTs have an average diameter of from about 150 nm to about 300 nm.

In one example composition, the CNTs have an average diameter of from about 200 nm to about 250 nm.

In one example composition, the surface features have an average high-point-to-high-point spacing of from about 500 nm to about 1100 nm.

In one example composition, the surface features have an average high-point-to-high-point spacing of from about 600 nm to about 1000 nm.

In one example there is provided a device, comprising a superhydrophobic surface, including a pyrolyzed carbon-infiltrated (C-I) carbon nanotube (CNT) layer having a contact angle greater than or equal to 150 degrees for a 0.05 mL droplet of water at room temperature, including a layer of CNTs, and a carbon infiltrant material infiltrated into the layer of CNTs to form a C-I CNT layer.

In one example device, the layer of CNTs extends from an underlying support substrate of the superhydrophobic surface.

In one example device, the layer of CNTs have been grown on the support substrate.

In one example device, CNTs for the layer of CNTs are grown separately from, and subsequently deposited onto, the support substrate.

In one example device, the carbon infiltrant material is infiltrated into and around CNTs of the layer of CNTs.

In one example device, the support substrate includes a member selected from the group consisting of metals, metal alloys, polymers, ceramics, semiconductors, and combinations thereof.

In one example device, the pyrolyzed C-I CNT layer further comprises a microbially-resistant topological pattern of surface features.

In one example device, the topological pattern of surface features has a structural configuration that limits microbial contact.

In one example device, the topological pattern of surface features has a surface feature density, wherein the surface feature density is sufficient to limit microbial contact and insufficient for the surface features to act as a microbial growth substrate.

In one example device, the device is a medical device.

In one example device, the medical device is selected from the group consisting of a surgical implement, an implantable device, an insertable device, a diagnostic device, a prosthetic device, a medical instrument, and combinations thereof.

In one example device, the device is an electronic device.

In one example device, the electronic device is selected from the group consisting of mobile phones, laptops, keyboards, mice, computer terminals, tablets, watches, touch screens, and game controllers.

In one example there is provided a method of making a superhydrophobic surface, comprising depositing a carbon nanotube (CNT) layer on a support substrate, infiltrating the CNT layer with a carbon infiltrant material to form a carbon infiltrated (C-I) CNT layer, and pyrolyzing the C-I CNT layer to form a pyrolyzed C-I CNT layer, wherein the resulting superhydrophobic surface has a contact angle greater than or equal to 150 degrees for a 0.05 mL droplet of water at room temperature.

In one example method, depositing the CNT layer further includes growing the CNTs on the support substrate.

In one example method, growing the CNTs on the support substrate further comprises growing the CNTs to an average height of from about 20 to about 75 microns from the support substrate.

In one example method, growing the CNTs on the support substrate further comprises growing the CNTs to an average height of from about 30 to about 50 microns from the support substrate.

In one example method, the carbon infiltrant material is infiltrated into and around CNTs of the layer of CNTs.

In one example method, infiltrating the CNT layer further comprises infiltrating the CNT layer to form the C-I CNT layer having a microbially-resistant topological pattern of surface features.

In one example method, the topological pattern of surface features has a structural configuration that limits microbial contact.

In one example method, the topological pattern of surface features has a surface feature density, wherein the surface feature density is sufficient to limit microbial contact and insufficient for the surface features to act as a microbial growth substrate.

In one example method, the CNTs have an average diameter of from about 150 nm to about 300 nm.

In one example method, the CNTs have an average diameter of from about 200 nm to about 250 nm.

In one example method, the surface features have an average high-point-to-high-point spacing of from about 500 nm to about 1100 nm.

In one example method, the surface features have an average high-point-to-high-point spacing of from about 600 nm to about 1000 nm.

In one example method, pyrolyzing the C-I CNT layer to form the pyrolyzed C-I CNT layer further comprises heating the C-I CNT layer in an oxygen-free environment for a sufficient time at a sufficient temperature to produce the pyrolyzed C-I CNT layer having a contact angle greater than or equal to 150 degrees for a 0.05 mL droplet of water at room temperature.

In one example method, the sufficient temperature is greater than or equal to 150 C.

In one example method, the sufficient temperature is from 600 C to 800 C.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by any claims associated with this or related applications.

What is claimed:

1. A superhydrophobic composition, comprising:
    a pyrolyzed carbon-infiltrated (C-I) carbon nanotube (CNT) layer having a contact angle greater than or equal to 150 degrees for a 0.05 mL droplet of water at room temperature, including:
    a layer of CNTs; and a carbon infiltrant material infiltrated into the layer of CNTs to form a C-I CNT layer.

2. The composition of claim 1, further comprising a support substrate upon which the pyrolyzed C-I CNT layer is supported.

3. The composition of claim 2, wherein the layer of CNTs have been grown on the support substrate.

4. The composition of claim 1, wherein the pyrolyzed C-I CNT layer further comprises a microbially-resistant topological pattern of surface features that limits microbial contact.

5. The composition of claim 4, wherein the topological pattern of surface features has a surface feature density, wherein the surface feature density is sufficient to limit microbial contact and insufficient for the surface features to act as a microbial growth substrate.

6. The composition of claim 4, wherein the CNTs have an average diameter of from about 150 nm to about 300 nm.

7. The composition of claim 4, wherein the surface features have an average high-point-to-high-point spacing of from about 500 nm to about 1100 nm.

8. A device, comprising:
a superhydrophobic surface, including;
a pyrolyzed carbon-infiltrated (C-I) carbon nanotube (CNT) layer having a contact angle greater than or equal to 150 degrees for a 0.05 mL droplet of water at room temperature, including:
a layer of CNTs; and
a carbon infiltrant material infiltrated into the layer of CNTs to form a C-I CNT layer.

9. The device of claim 8, wherein the layer of CNTs extends from an underlying support substrate of the superhydrophobic surface.

10. The device of claim 9, wherein the carbon infiltrant material is infiltrated into and around CNTs of the layer of CNTs.

11. The device of claim 9, wherein the pyrolyzed C-I CNT layer further comprises a microbially-resistant topological pattern of surface features that limits microbial contact.

12. The device of claim 11, wherein the topological pattern of surface features has a surface feature density, wherein the surface feature density is sufficient to limit microbial contact and insufficient for the surface features to act as a microbial growth substrate.

13. The device of claim 8, wherein the device is a medical device.

14. The device of claim 13, wherein the medical device is selected from the group consisting of a surgical implement, an implantable device, an insertable device, a diagnostic device, a prosthetic device, a medical instrument, and combinations thereof.

15. The device of claim 8, wherein the device is an electronic device selected from the group consisting of mobile phones, laptops, keyboards, mice, computer terminals, tablets, watches, touch screens, and game controllers.

16. A method of making a superhydrophobic surface, comprising:
depositing a carbon nanotube (CNT) layer on a support substrate;
infiltrating the CNT layer with a carbon infiltrant material to form a carbon infiltrated (C-I) CNT layer; and
pyrolyzing the C-I CNT layer to form a pyrolyzed C-I CNT layer;
wherein the resulting superhydrophobic surface has a contact angle greater than or equal to 150 degrees for a 0.05 mL droplet of water at room temperature.

17. The method of claim 16, wherein depositing the CNT layer further includes growing the CNTs on the support substrate.

18. The method of claim 17, wherein growing the CNTs on the support substrate further comprises growing the CNTs to an average height of from about 20 to about 75 microns from the support substrate.

19. The method of claim 16, wherein infiltrating the CNT layer further comprises infiltrating the CNT layer to form the C-I CNT layer having a microbially-resistant topological pattern of surface features that limits microbial contact.

20. The method of claim 16, wherein pyrolyzing the C-I CNT layer to form the pyrolyzed C-I CNT layer further comprises:
heating the C-I CNT layer in an oxygen-free environment for a sufficient time at a sufficient temperature to produce the pyrolyzed C-I CNT layer having a contact angle greater than or equal to 150 degrees for a 0.05 mL droplet of water at room temperature.

21. The method of claim 20, wherein the sufficient temperature is greater than or equal to 150 C.

22. The method of claim 20, wherein the sufficient temperature is from 600 C to 800 C.

* * * * *